United States Patent
Pointillart et al.

(10) Patent No.: US 8,821,577 B2
(45) Date of Patent: Sep. 2, 2014

(54) INTERVERTEBRAL DISK PROSTHESIS

(75) Inventors: Vincent Pointillart, Rue Naujac (FR); Richard Assaker, Kain (BE)

(73) Assignees: Richard Assaker, Kain (BE); Vincent Pointillart, Bordeaux (FR)

( * ) Notice: Subject to any disclaimer, the term of this patent is extended or adjusted under 35 U.S.C. 154(b) by 1188 days.

(21) Appl. No.: 12/093,845

(22) PCT Filed: Nov. 14, 2006

(86) PCT No.: PCT/FR2006/002515
§ 371 (c)(1),
(2), (4) Date: Mar. 4, 2009

(87) PCT Pub. No.: WO2007/057555
PCT Pub. Date: May 24, 2007

(65) Prior Publication Data
US 2009/0228109 A1     Sep. 10, 2009

(30) Foreign Application Priority Data
Nov. 16, 2005   (FR) ...................................... 05 11596

(51) Int. Cl.
A61F 2/44 (2006.01)
A61F 2/30 (2006.01)

(52) U.S. Cl.
CPC ......... *A61F 2/442* (2013.01); *A61F 2220/0025* (2013.01); *A61F 2/30742* (2013.01); *A61F 2002/30462* (2013.01); *A61F 2220/0075* (2013.01); *A61F 2002/30476* (2013.01); *A61F 2002/30383* (2013.01); *A61F 2250/0008* (2013.01); *A61F 2002/30682* (2013.01); *A61F 2002/30471* (2013.01); *A61F 2220/0091* (2013.01); *A61F 2002/30553* (2013.01); *A61F 2002/30563* (2013.01); *A61F 2/30771* (2013.01)

USPC ...................................... 623/17.16; 623/17.11

(58) Field of Classification Search
USPC ............. 606/248, 249, 246; 623/17.11–17.16
See application file for complete search history.

(56) References Cited

U.S. PATENT DOCUMENTS

| | | | | |
|---|---|---|---|---|
| 6,093,205 A | * | 7/2000 | McLeod et al. | 623/17.16 |
| 6,582,466 B1 | * | 6/2003 | Gauchet | 623/17.11 |
| 7,250,060 B2 | | 7/2007 | Trieu | |
| 7,905,922 B2 | * | 3/2011 | Bergeron | 623/17.16 |
| 2003/0187506 A1 | | 10/2003 | Ross et al. | |
| 2004/0049279 A1 | * | 3/2004 | Sevrain | 623/17.13 |
| 2004/0059418 A1 | * | 3/2004 | McKay et al. | 623/17.16 |
| 2005/0165485 A1 | * | 7/2005 | Trieu | 623/17.13 |
| 2006/0069436 A1 | * | 3/2006 | Sutton et al. | 623/17.13 |
| 2006/0089721 A1 | * | 4/2006 | Muhanna et al. | 623/17.16 |

FOREIGN PATENT DOCUMENTS

| | | |
|---|---|---|
| JP | HEI2307494 A2 | 12/1990 |
| JP | 2008504892 A | 2/2008 |
| WO | 2005072660 A1 | 8/2005 |
| WO | 2006004848 A1 | 1/2006 |

* cited by examiner

*Primary Examiner* — Pedro Philogene
*Assistant Examiner* — Christina Negrellirodrigue
(74) *Attorney, Agent, or Firm* — Muncy, Geissler, Olds & Lowe, P.C.

(57) ABSTRACT

An intervertebral disk prosthesis (4), comprising:
  a rigid top plate (5);
  a rigid bottom plate (6); and
  an elastically-compressible intermediate cushion (7) received between the two inside surfaces of the plates (5, 6); remarkable in that the assembly is subdivided in the thickness direction into two units resting one on the other via complementary contact surfaces.

3 Claims, 2 Drawing Sheets

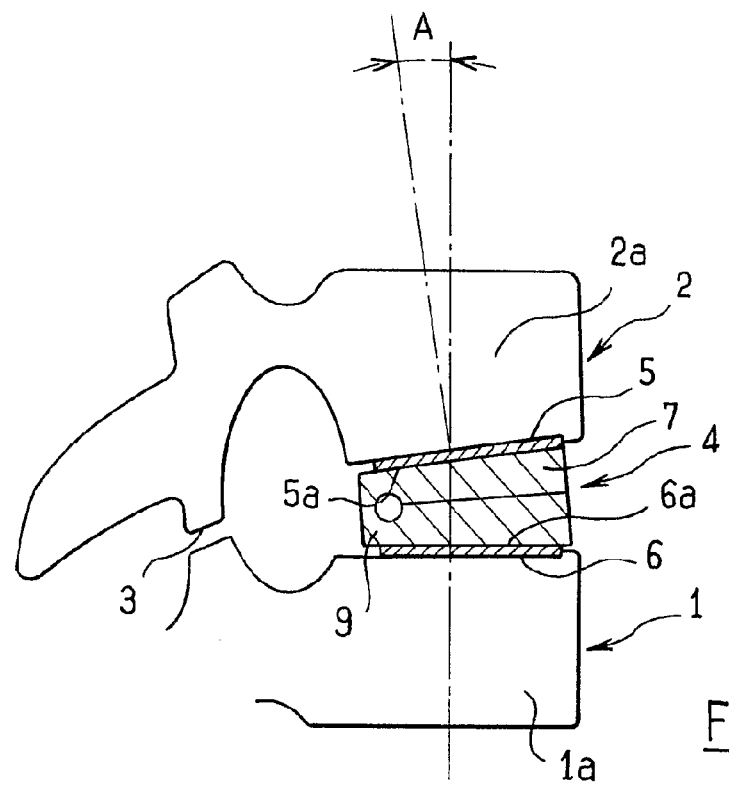
FIG_1
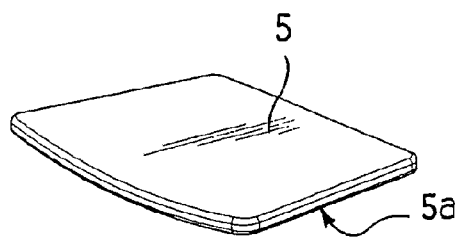
FIG_2
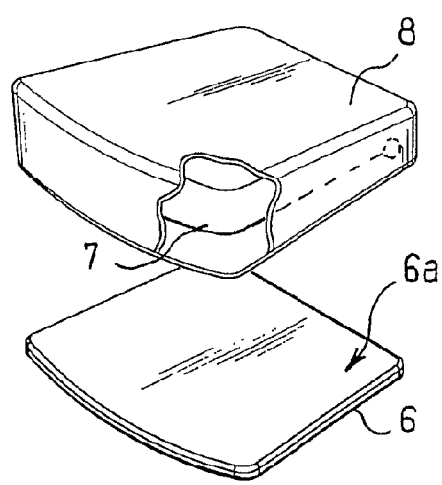
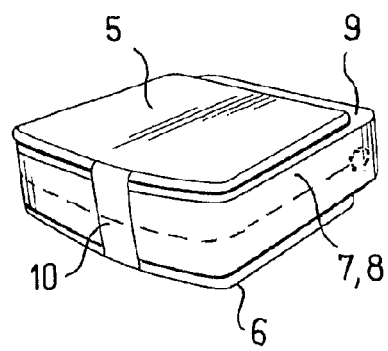
FIG_3

INTERVERTEBRAL DISK PROSTHESIS

The invention relates to an intervertebral disk prosthesis for replacing in full or in part the natural disks that provide the connection between two vertebrae of the vertebral column, regardless of the portion of the spine that is concerned.

BACKGROUND OF THE INVENTION

Each intervertebral disk of the vertebral column is constituted by a central element referred to as the nucleus pulposus that is enclosed in a winding of fibers referred to as the annulus. The disk provides a connection between two vertebral bodies and it controls the flexing, bending, and turning movements of the vertebral column. Such a disk can become damaged under the effect of time, effort, or certain degenerative diseases, and it then becomes flattened and/or ceases to function properly. This can lead to various types of pathology, leading to multiple more or less intense pains and to handicaps of greater or lesser extent.

Treatment for that type of disorder consists in removing the diseased disk and replacing it either with an element that is movable or deformable, or with an element that readily interconnects the two vertebrae concerned.

Several type of prosthesis have been proposed for replacing an intervertebral disk, however they are satisfactory in part only. They do indeed preserve mobility between vertebrae and restore the distance between the vertebrae to a value close to that provided by a healthy disk. However, in providing such mobility, they impose particular dynamics that are not compatible or that are only partially compatible with the natural relative mobility between two vertebrae. In most circumstances, the prosthesis imposes dynamics that are specific thereto, with its center of rotation and its various plane-on-plane guidances, and that inevitably interfere with the natural joint elements that remain between two vertebrae, in particular the posterior articular facets. In this respect it is important to position the prosthesis with care since any inaccuracy in such placement increases the severity of the conflict between the dynamics of the prosthesis and natural dynamics. This non-physiological mobility can lead to undesirable clinical consequences. It is even possible that a component might migrate or that the prosthesis might become dislocated.

Furthermore, most known prostheses are unsuitable for restoring normal cervical or lumbar lordosis. Restoring the distance between vertebrae does not take account of the inclinations needed from one vertebra to the next in the stack of vertebrae in order to attain such natural lordosis, the existence of which is useful for normal biomechanics of the spine as a whole, and in particular of the adjacent levels.

Furthermore, known prostheses are not adapted to absorb shocks. A consequence of this unsuitability, associated with the conflict between the natural dynamics and the dynamics of the joint, can lead to premature wear both in natural elements and in elements of the prosthesis, thereby running the risk of degrading the patient's clinical state.

OBJECT OF THE INVENTION

The present invention seeks to remedy those drawbacks by a disk prosthesis of simple structure and that is easy to put into place.

SUMMARY OF THE INVENTION

To this end, the present invention provides an intervertebral disk prosthesis comprising:

a rigid top plate;
a rigid bottom plate; and
an elastically-compressible intermediate cushion received between the two inside surfaces of the plates;
the assembly having the feature of being subdivided in the thickness direction into two units resting one on the other via complementary contact surfaces.

This structure is in the form of a part that does not impose any stressed connection between the two vertebrae it connects together (naturally this applies to amplitudes corresponding to natural relative movements). As a result, the natural guides for guiding such relative movements remain preponderant (in particular the posterior articular facets), and their integrity is preserved. In addition, at these contact surfaces, it is possible, by making an appropriate selection for their shape and their state, to govern the nature and the concentration of the stresses and the deformations that occur at said surfaces.

In a first embodiment of the invention, the complementary contact surfaces are formed in the thickness of the intermediate cushion, and preferably in the form of indentations and projections (teeth), the projections of one of them being complementary to the indentations of the other, so that they come into contact with each other over via least the surfaces of their flanks.

In a preferred embodiment of the invention, the elastically compressible intermediate cushion housed between the two inside surfaces of the plates possesses, in the free state, the general shape of a wedge between said two plates. This wedge shape of the structure enables the lordosis of the spine to be restored, which lordosis will generally have been degraded by the degeneration of the disk.

By way of example, the cushions may be based on high density polyethylenes, on high density polyurethanes, on silicones, or on composites of those various materials.

The prosthesis preferably includes a contention membrane for the cushion, which membrane is secured to the plates. The contention membrane serves to avoid biological invasion and colonization of the prosthesis. It also serves, in spite of all of the materials used being biocompatible, to isolate the cushion completely from the adjacent biological medium, and it forms a barrier to migration into the organism of any particles that might come from the cushion.

The membrane may be an annulus that is to be fastened to the plates (leaving direct contact between the cushion and each plate), or it may be a hermetically-sealed bag, enclosing the cushion, and for example bonded to the plates by adhesive, or indeed it may be a membrane that is sandwiched between each plate and a backing plate that is riveted thereto, the other face of the backing plate being in contact with the cushion.

Other structural arrangements appear on reading the description below. Particular mention can be made of the existence of a tie between the two plates of the prosthesis that enables the prosthesis to be kept in a compressed state so as to make it easier to put into place. One of the advantages of the prosthesis lies in that it is easy to put into place, and that this does not require great accuracy since there is no need to "match" its degrees of freedom with the natural degrees of freedom that exist between two vertebrae.

BRIEF DESCRIPTION OF THE DRAWINGS

Other characteristics and advantages of the invention appear from the description given below of a few embodiments thereof.

DETAILED DESCRIPTION OF THE INVENTION

Figure 4:
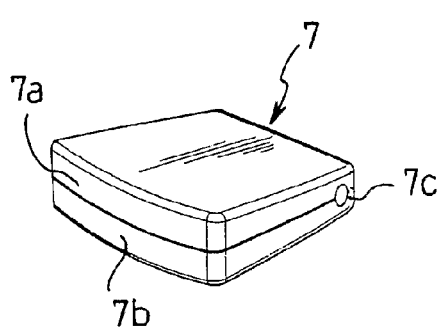
Figure 5:
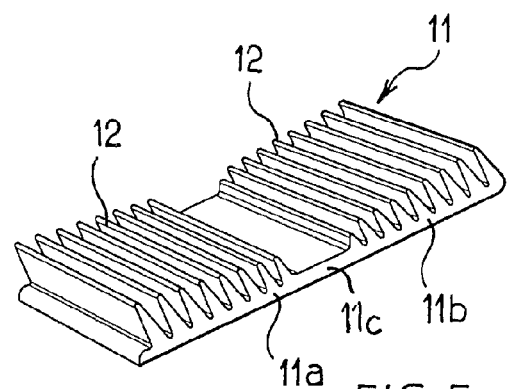
Figure 6:
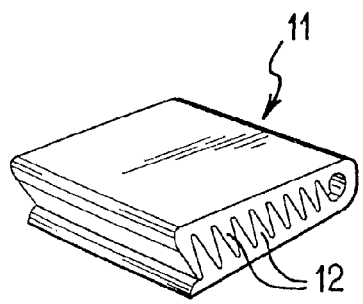
Figure 7:
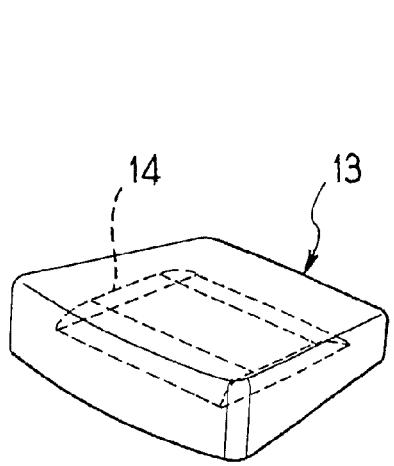

Reference is made to the accompanying drawings, in which:

FIG. 1 shows a prosthesis of the invention placed between two cervical vertebrae;

FIG. 2 is an exploded view of an embodiment of a prosthesis in accordance with the invention;

FIG. 3 is a view of the FIG. 2 prosthesis when closed and held compressed by a severable tie;

FIG. 4 shows an embodiment of the compressible cushion;

FIG. 5 shows a variant embodiment of the compressible cushion of the preceding figure;

FIG. 6 shows the cushion of the preceding figure folded in half;

FIG. 7 shows a variant embodiment of a compressible cushion; and

Figure 8:
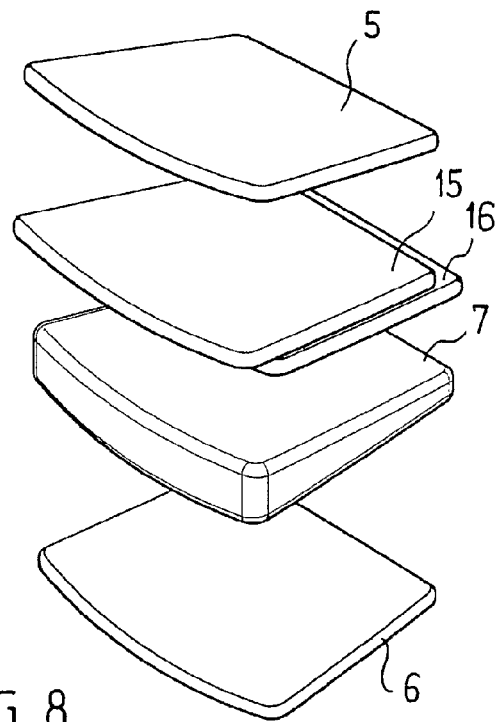

FIG. 8 is an exploded view of a variant embodiment of the prosthesis of the invention.

DETAILED DESCRIPTION OF THE INVENTION

FIG. 1 shows two successive cervical vertebrae 1 and 2, each having a vertebral body 1a and 2a, and a posterior articular surface 3. Between the vertebral bodies, there is shown in diagrammatic manner a prosthesis 4 comprising two end plates 5 and 6 together with an intermediate body 7 in the form of a compressible cushion that is wedge-shaped with the tip or vertex (thin end) in the posterior position, the right-hand portion of the figure representing the anterior zone of the spine.

The end plates 5 and 6 of the prosthesis are in contact with the vertebral bodies 1a and 2a via surfaces of said bodies that have received prior preparation after removal of the damaged natural disk. The outside surfaces of these plates may include anchor means, e.g. portions in relief, in order to improve bone fixing; they may also make use of screws or any other equivalent element. The spine is shown presenting lordosis through an angle A that imposes on the prosthesis the relative orientation of these two vertebrae.

In FIG. 2, it can be seen that each of the plates 5 and 6 possesses an inside surface 5a, 6a, drawn as plane, but that could possibly have a substantially spherical or cylindrical concave shape. The compressible cushion 7 is fastened to the plate. This cushion is enclosed in a contention membrane 8 that biologically isolates the cushion from the remainder of the patient's body. The membrane is fastened to the remainder of the prosthesis by any appropriate means. By way of example, mention can be made of a "cylindrical" membrane fastened to the edge of each plate (in particular by crimping); the membrane may also be such that its edge is sandwiched between the inside face of each plate and a backing plate fitted thereto, e.g. by riveting. The membrane may also be in the form of a completely closed bag with the plates being stuck thereto.

FIG. 3 shows the prosthesis in its state ready for being inserted between two vertebrae, this state corresponding to the compressible cushion 7 being held in a compressed state by a tie 10 disposed on the anterior face of the prosthesis 4 and that is suitable for being ruptured after the prosthesis has been put into place between the vertebral bodies 1a and 2a. The tie may also be placed in such a manner as to surround the entire prosthesis so that it can be ruptured and removed after being cut, when necessary, by the surgeon acting via a posterior approach.

In this figure, it can be seen that the plates 5 and 6 are of dimensions such that, in the posterior portion of the prosthesis, they are set back from the cushion which projects beyond the plates via a portion 9 beside the tip of the wedge.

FIG. 4, as a detail corresponding to the preceding figures, shows an elastically compressible cushion 7 that is folded in half, having two portions 7a and 7b folded one onto the other about a portion 7c that constitutes a thin zone forming a folding hinge that becomes the posterior end of the wedge. The prosthesis is thus subdivided into two units that co-operate with each other via complementary contact surfaces, here represented diagrammatically as being plane surfaces.

In FIG. 5, the cushion 11 shown likewise possesses two membranes 11a and 11b that can be folded one onto the other about a thin zone 11c acting as a folding hinge, such that, as shown in FIG. 6, indentations 12 can interpenetrate when the two portions are folded one against the other. It can be understood that the contact surface via which the two units of the prosthesis co-operate is complex in this embodiment: it comprises the flanks of interpenetrating teeth. On fabrication, it is possible to select the angle of inclination of the indentations 12, the number of indentations, their profile, . . . as a function of the elastic characteristics and of the behavior desired for the cushion.

In a variant (not shown) the indentations are curved, e.g. in circular arcs centered beside the hinge.

In another variant (not shown) the two portions 11a and 11b can be separate (the hinge being omitted) and merely superposed with their indentations interleaved.

In FIG. 7, the cushion 13 as shown constitutes a kind of resilient capsule for a gel core 14 that can deform depending on the extent to which the cushion is compressed during intervertebral movements. In this embodiment, the prosthesis likewise satisfies the general definition of the invention, i.e. the lens of gel subdivides the prosthesis into two units possessing surfaces that co-operate with each other via a gel. In other words, the functional complementarity of the surfaces is provided by the gel lens.

Finally, FIG. 8 shows a variant embodiment of the prosthesis reproducing most of the elements described above and given the same references. Inside the membrane (not shown), this variant embodiment has two slide tabs 15 and 16 situated in the vicinity of one of the plates, between the cushion and that plate. The subdivision of the prosthesis into two units is performed in this embodiment outside the cushion, the complementary surfaces being slide planes with surface states prepared so as to correspond with desired behavior. The cushion is shown as being a single piece. It could also be made as two portions folded one on the other, with the ability to slide being in additional to the performance of the prosthesis that results from it being separated into two units as described above.

Advantageously, at least one of the plates 5 and 6, and preferably both of them, is dimensioned in such a manner that the prosthesis has a cushion that projects beyond the plates, behind them, so as to leave a space adjacent to the posterior portion of the spine in which there is no metal element, with this being done for two purposes:

limiting the artifact (degraded imagery) concerning this posterior portion of the spine by keeping the metal portion constituted by the plate away therefrom; and facilitating decompression (resection of the posterior wedges of the vertebral plates).

Finally, it should be mentioned that the above-described prosthesis corresponds to a single-piece prosthesis that is put into place using an anterior approach. In an embodiment adapted to be put into place via a posterior approach, it would comprise two half-prostheses that are put into place via lateral approaches so as to be placed on either side of the remaining portion (nucleus pulposus) of the natural disk. The shape of each half-prosthesis should then be adapted to the morphology that is encountered, e.g. by being kidney-bean shaped, when seen from above. Each half-prosthesis should be subdivided into two units using the various above-described variants.

What is claimed is:

1. An intervertebral disk prosthesis (4), comprising:
a rigid top plate (5);
a rigid bottom plate (6); and
an elastically-compressible continuous intermediate cushion (7) received between two inside surfaces of the plates (5, 6), the intermediate cushion comprises two portions and a thin zone connecting the two portions, the thin zone forms a folding hinge so that the two portions can fold onto the other, wherein the folding hinge becomes a posterior end of the prosthesis;
wherein the prosthesis is subdivided in a thickness direction into two units resting one on the other via complementary contact surfaces, and
wherein the prosthesis includes a contention membrane (8) for the cushion (7), which membrane is secured to the plates (5, 6).

2. An intervertebral disk prosthesis (4), comprising:
a rigid top plate (5);
a rigid bottom plate (6); and
an elastically-compressible continuous intermediate cushion (7) received between two inside surfaces of the plates (5, 6), the intermediate cushion comprises two portions and a thin zone connecting the two portions, the thin zone forms a folding hinge so that the two portions can fold onto the other, wherein the folding hinge becomes a posterior end of the prosthesis;
wherein the prosthesis is subdivided in a thickness direction into two units resting one on the other via complementary contact surfaces, and
wherein the prosthesis includes a tie (10) for holding the cushion in a compressed state, and suitable for being severed after the prosthesis has been put into place.

3. An intervertebral disk prosthesis (4), comprising:
a rigid top plate (5);
a rigid bottom plate (6); and
an elastically-compressible continuous intermediate cushion (7) received between two inside surfaces of the plates (5, 6), the intermediate cushion comprises two portions and a thin zone connecting the two portions, the thin zone forms a folding hinge so that the two portions can fold onto the other, wherein the folding hinge becomes a posterior end of the prosthesis;
wherein the prosthesis is subdivided in a thickness direction into two units resting one on the other via complementary contact surfaces, and
wherein the complementary contact surfaces of the two units are provided with interleaved indentations (12).

* * * * *